United States Patent
Wagner

(10) Patent No.: US 11,963,903 B1
(45) Date of Patent: Apr. 23, 2024

(54) ORAL APPLIANCES WITH PALATE EXTENSION

(71) Applicant: SLOW WAVE, INC., Spicewood, TX (US)

(72) Inventor: Wayne R. Wagner, Spicewood, TX (US)

( * ) Notice: Subject to any disclaimer, the term of this patent is extended or adjusted under 35 U.S.C. 154(b) by 0 days.

(21) Appl. No.: 18/502,514

(22) Filed: Nov. 6, 2023

Related U.S. Application Data

(63) Continuation of application No. 18/155,872, filed on Jan. 18, 2023, now Pat. No. 11,806,274.

(60) Provisional application No. 63/379,758, filed on Oct. 16, 2022.

(51) Int. Cl.
*A61F 5/56* (2006.01)

(52) U.S. Cl.
CPC .................. *A61F 5/566* (2013.01)

(58) Field of Classification Search
CPC ...... A61F 5/56; A61F 5/566; A61F 2005/563; A63B 2071/086; A63B 2071/088; A63B 71/085; A61C 7/08; A61C 7/36; A61C 7/10
See application file for complete search history.

(56) References Cited

U.S. PATENT DOCUMENTS

| | | | |
|---|---|---|---|
| 3,132,647 A | 5/1964 | Corniello | |
| 3,217,708 A * | 11/1965 | Roberts | A63B 71/085 |
| | | | 600/237 |
| 3,434,470 A | 3/1969 | Strickland | |
| 4,304,227 A | 12/1981 | Samelson | |
| 4,396,373 A | 8/1983 | Dellinger | |

(Continued)

FOREIGN PATENT DOCUMENTS

| | | |
|---|---|---|
| EP | 1205157 A1 | 5/2002 |
| EP | 1203570 B1 | 11/2011 |

(Continued)

OTHER PUBLICATIONS

Bailey, Premarket Notification [510(k)] Summary K013049 for mandibular repositioning appliance (device) known as NOrAD(TM), clearance granted by United States FDA, Nov. 29, 2001.

(Continued)

*Primary Examiner* — Camtu T Nguyen
(74) *Attorney, Agent, or Firm* — Jeffrey L. Wendt; The Wendt Firm, P.C.

(57) ABSTRACT

Apparatus for reducing obstructive sleep apnea, snoring and/or nasal drainage, or improving sleep quality. One apparatus includes an upper member fitting portions of the interior and exterior surfaces of a user's upper dentition, and a lower member fitting similarly adjacent a user's lower dentition. The upper and lower members include molar and pre-molar extensions so that when the user bites or clenches, the upper right and lower right extensions impinge on one another in substantially overlapping fashion, as do the upper left and lower left extensions. The upper member includes a palate extension that extends posteriorly from the upper member in the region of the upper incisors, which introduces a tongue resting spot to compensate for the lowering of the mandible and restoring the proper tongue posture while sleeping. The oral devices may be produced by additive or subtractive manufacturing methods.

20 Claims, 8 Drawing Sheets

(56) References Cited

U.S. PATENT DOCUMENTS

| | | |
|---|---|---|
| 4,531,916 A | 7/1985 | Scantlebury et al. |
| 4,671,767 A | 6/1987 | Blechman et al. |
| 4,676,240 A | 6/1987 | Gardy |
| 4,700,697 A | 10/1987 | Mundell et al. |
| 4,708,646 A | 11/1987 | Jasper |
| 4,715,368 A | 12/1987 | George |
| 4,901,737 A | 2/1990 | Toone |
| 5,013,243 A | 5/1991 | Tanaka et al. |
| 5,056,534 A | 10/1991 | Wright |
| 5,117,816 A | 6/1992 | Shapiro et al. |
| 5,239,995 A | 8/1993 | Estes et al. |
| 5,499,633 A | 3/1996 | Fenton |
| RE35,295 E | 7/1996 | Estes et al. |
| 5,570,704 A | 11/1996 | Buzzard et al. |
| 5,611,355 A | 3/1997 | Hilsen |
| 5,678,998 A | 10/1997 | Honkura et al. |
| 5,683,244 A | 11/1997 | Truax |
| 5,692,521 A | 12/1997 | Leasure-Nelson |
| 6,074,207 A | 6/2000 | Coats |
| 6,082,363 A | 7/2000 | Washburn |
| 6,109,265 A | 8/2000 | Frantz et al. |
| 6,213,959 B1 | 4/2001 | Kushida |
| 6,299,450 B1 | 10/2001 | Honkura et al. |
| 6,427,689 B1 | 8/2002 | Estes |
| 6,491,037 B1 | 12/2002 | Mortenson |
| 6,505,625 B1 | 1/2003 | Uenishi |
| 6,659,771 B2 | 12/2003 | Honkura et al. |
| 6,766,802 B1 | 7/2004 | Keropian |
| 7,107,992 B2 | 9/2006 | Brooks et al. |
| 7,178,529 B2 | 2/2007 | Kownacki |
| 7,225,021 B1 | 5/2007 | Park et al. |
| 7,255,110 B2 | 8/2007 | Knudson et al. |
| 7,322,356 B2 | 1/2008 | Critzer et al. |
| 7,451,767 B2 | 11/2008 | Keropian |
| 7,540,843 B2 | 6/2009 | De Backer |
| 7,607,439 B2 | 10/2009 | Li |
| 7,637,262 B2 | 12/2009 | Bailey |
| 7,712,468 B2 | 5/2010 | Hargadon |
| 7,810,502 B1 | 10/2010 | Nguyen et al. |
| 8,061,358 B2 | 11/2011 | Smernoff |
| 8,215,312 B2 | 7/2012 | Garabadian et al. |
| 8,257,079 B1 | 9/2012 | Plowman |
| 8,272,866 B2 | 9/2012 | Chun et al. |
| 8,875,713 B2 | 11/2014 | Metz |
| 8,881,733 B1 | 11/2014 | Harkins |
| 9,144,512 B2 | 9/2015 | Wagner |
| 9,204,991 B1 | 12/2015 | Harkins |
| 9,408,743 B1 | 8/2016 | Wagner |
| 9,439,802 B2 | 9/2016 | Wagner |
| 9,445,938 B1 | 9/2016 | Wagner |
| 10,299,957 B2 | 5/2019 | Wagner |
| 11,273,071 B2 | 3/2022 | Wagner |
| 11,806,274 B1 * | 11/2023 | Wagner ............ A61F 5/566 |
| 2001/0027793 A1 | 10/2001 | Tielemans |
| 2004/0177852 A1 | 9/2004 | Abramson |
| 2005/0121039 A1 | 6/2005 | Brooks et al. |
| 2005/0236003 A1 | 10/2005 | Meader |
| 2006/0252685 A1 | 11/2006 | Gould |
| 2006/0289013 A1 | 12/2006 | Keropian |
| 2007/0283967 A1 * | 12/2007 | Bailey ............ A61F 5/566 |
| | | 128/848 |
| 2008/0060660 A1 | 3/2008 | Nelson et al. |
| 2008/0173312 A1 | 7/2008 | Peake et al. |
| 2008/0199824 A1 | 8/2008 | Hargadon |
| 2008/0210244 A1 | 9/2008 | Keropian |
| 2008/0257358 A1 | 10/2008 | Stern et al. |
| 2008/0264422 A1 | 10/2008 | Fishman |
| 2008/0276938 A1 | 11/2008 | Jeppeson et al. |
| 2009/0036889 A1 | 2/2009 | Callender |
| 2009/0056724 A1 | 3/2009 | Keropian |
| 2009/0120448 A1 | 5/2009 | Keropian |
| 2009/0188510 A1 | 7/2009 | Palmer |
| 2010/0211184 A1 | 8/2010 | Rousseau et al. |
| 2010/0224197 A1 | 9/2010 | Keropian |
| 2010/0300458 A1 | 12/2010 | Stubbs et al. |

FOREIGN PATENT DOCUMENTS

| | | |
|---|---|---|
| WO | WO 2007/134375 | 11/2007 |
| WO | WO 2010/040026 | 4/2010 |
| WO | WO 2010/062952 | 6/2010 |
| WO | WO 2010/093264 | 8/2010 |

OTHER PUBLICATIONS

Bailey, Premarket Notification [510(k)] Summary K020893 for mandibular repositioning appliance (device) known as NOrAD(TM), clearance granted by United States FDA, May 28, 2002.

Britishsnoring; Tomed SomnoGuard FittingHeated for 20 seconds, YouTube video, uploaded to the Internet by britishsnoring on Jul. 27, 2017, https://www.youtube.com/watch?v=NNe8eZeo3TQ.

Department of Health & Human Services; K964516; Letter to James Bonds of Nellcor Puritan Bennett, Incorporated; Jun. 2, 2005; Rockville, Md; US.

Dynasplint; Wearing your Jaw Dynasplint® System, YouTube video, uploaded to the Internet by dynasplint on Oct. 5, 2011, https://www.youtube.com/watch?v=3hjP24aByd4.

European Patent Office; "Invitation to Pay Additional Fees and, Where Applicable, Protest Fee" for PCT/US2012/036474; Jul. 25, 2012; Rijswijk; Netherlands.

European Patent Office; International Search Report for PCT/US2012/036474; 6 pages, Sep. 9, 2012; Rijswijk, Netherlands.

European Patent Office; Written Opinion of the International Searching Authority for PCT/US2012/036474, 12 pages, Sep. 9, 2012; Munich, Germany.

FDA 510(k) Summary K033822, Feb. 6, 2004.

FDA 510(k) Summary K033823, Feb. 6, 2004.

FDA 510(k) Summary K042161, Oct. 27, 2004.

FDA 510(k) Summary K061688, Sep. 8, 2006.

FDA 510(k) Summary K102118, Sep. 8, 2010; Ranir, LLC, 510(k) Summary K102118 for Intraoral Anti-Snoring Device known as Snore Guard Advance(TM), clearance granted by United States FDA, Sept. 8, 2010.

FDA 510(k) Summary K121761, Sep. 28, 2012.

FDA 510(k) Summary K962516, Sep. 10, 1996.

FDA 510(k) Summary K972061, Aug. 21, 2007; Thornton; Non-Confidential Summary of Safety and Effectiveness; K972061; Aug. 21, 1997; Dallas, TX; US.

FDA 510(k) Summary; Wagner Direct; FDA 501K Summary; Apr. 15, 2014; Houston, Texas; US.

Hoffstein; "Review of oral appliances for treatment of sleep-disordered breathing", Sleep Breath (2007) 11 :1-22, published online Nov. 29, 2006, Springer-Verlag; Germany.

Houston-Chronicle; "Tired of Your CPAP?", Jan. 16, 2011.

I Hate Crap !; "Sleep Apnea Appliances, I Hate CPAP!", p. 1-8, downloaded from the Internet Oct. 25, 2010; http://www.ihatecpap.com/oral_appliances.html'; Illinois; US.

Landers, SJ, "Link strengthened between sleep apnea and mortality risk", amednews, Sept. 1, 2008; American Medical Association; US.

Pancer, et al., "Evaluation of Variable Mandibular Advancement Appliance for Treatment of Snoring and Sleep Apnea", Chest (1999); 116:1511-1518; Clinical Investigations; US.

Prehn, Ronald S "What is a Mandibular Advancement Splint and How Does it Work?", YouTube video, uploaded to the Internet by rsprehn on Mar. 4, 2010, http://www.youtube.com/watch?v=OWiQQF4xQZc.

Randerath et al., "Non-CPAP therapies in obstructive sleep apnea", Eur Respir J (no month, 2011); vol. 37, No. 5; pp. 1000-1028; Paris, France.

Sybron Dental Specialties; 510(k) Summary K070327 for Intraoral Devices for Snoring and Intraoral Devices for Snoring and Obstructive Sleep Apnea known as Removable Acrylic Herbst(TM), Allesee Snore Appliance(TM), and Enoch Snorinator(TM), clearance granted by United States FDA, May 25, 2007; Sturtevant, WI; US.

Somnomed; Sleep Apnea Appliances; I hate CPAP; Oct. 25, 2010; 8 pages; US.

Response to Office Action for U.S. Appl. No. 14/852,768, filed Jun. 13, 2016, with Terminal Disclaimer; 7 pages.

(56) References Cited

OTHER PUBLICATIONS

Office Action for U.S. Appl. No. 14/852,768 issued Jun. 3, 2016; 8 pages.
Amendment after Allowance for U.S. Appl. No. 13/456,682, filed Aug. 15, 2015; 7 pages.
Amendment and Response for U.S. Appl. No. 13/456,682, filed Feb. 18, 2015; 17 pages.
Office Action for U.S. Appl. No. 13/456,682 issued Dec. 17, 2014; 15 pages.
Notice of Allowance and Fees Due with Notice of Allowability for U.S. Appl. No. 14/189,772 issued Jun. 24, 2016; 7 pages.
Amendment and Response for U.S. Appl. No. 14/189,772, filed May 17, 2016; 6 pages.
Office Action for U.S. Appl. No. 14/189,772 issued May 3, 2016; 8 pages.
Supplemental Amendment for U.S. Appl. No. 14/189,772, filed Mar. 17, 2016; 14 pages.
Amendment for U.S. Appl. No. 14/189,772, filed Jan. 22, 2016; 20 pages.
Amendment and Response for U.S. Appl. No. 14/189,772, filed Jun. 27, 2015; 20 pages.
Office Action issued for U.S. Appl. No. 14/189,772 on Apr. 27, 2015; 20 pages.
Notice of Allowance and Fee Due with Notice of Allowability for U.S. Appl. No. 15/005,116 issued Aug. 10, 2016; 7 pages.
Amendment and Response for U.S. Appl. No. 15/005,116, filed Jul. 18, 2016, with Terminal Disclaimer; 4 pages.
USPTO Office Action issued for U.S. Appl. No. 15/005,116 on Jul. 13, 2016; 11 pages.
USPTO Office Action issued for U.S. Appl. No. 15/251,902 on Oct. 3, 2018; 51 pages.
Response for U.S. Appl. No. 15/251,902, filed Jan. 3, 2019, with 2 Terminal Disclaimers; 3 pages.
USPTO Notice of Allowance and Fee Due with Notice of Allowability for U.S. Appl. No. 15/251,902 issued Feb. 19, 2019; 20 pages.
USPTO Office Action issued for U.S. Appl. No. 16/416,234 on Oct. 26, 2021; 68 pages.
Response for U.S. Appl. No. 16/416,234, filed Nov. 3, 2021, with 2 Terminal Disclaimers; 3 pages.
USPTO Notice of Allowance and Fee Due with Notice of Allowability for U.S. Appl. No. 16/416,234 issued Dec. 2, 2021; 69 pages.
USPTO Office Action issued for U.S. Appl. No. 17/695,373 on Feb. 3, 2023; 75 pages.

* cited by examiner

Before

After

ORAL APPLIANCES WITH PALATE EXTENSION

CROSS-REFERENCE TO RELATED APPLICATIONS

This application claims benefit under 35 USC 120 to U.S. nonprovisional patent application Ser. No. 18/155,872, filed Jan. 18, 2023, now U.S. Pat. No. 11,806,274, which in turn claims benefit under 35 USC 119 to U.S. provisional application No. 63/379,758, filed Oct. 16, 2022, both of which are incorporated herein by reference in their entirety, and may be related to the following U.S. application numbers and U.S. Patents, all of which are incorporated herein by reference in their entirety:

Ser. No. 13/456,682, filed Apr. 26, 2012, now U.S. Pat. No. 9,144,512;
Ser. No. 14/189,772, filed Feb. 25, 2014, now U.S. Pat. No. 9,408,743;
Ser. No. 14/852,768, filed Sep. 14, 2015, now U.S. Pat. No. 9,439,802;
Ser. No. 15/005,116, filed Jan. 25, 2016, now U.S. Pat. No. 9,445,938;
Ser. No. 15/251,902, filed Aug. 30, 2016, now U.S. Pat. No. 10,299,957;
Ser. No. 16/416,234, filed May 19, 2019, now U.S. Pat. No. 11,273,071;
Ser. No. 16/912,367, filed Jun. 25, 2020, now U.S. Pat. No. 11,813,192; and
Ser. No. 17/695,373, filed Mar. 15, 2022, now U.S. Pat. No. 11,779,486.

BACKGROUND INFORMATION

Technical Field

The present disclosure relates to oral appliances for reducing or eliminating obstructive sleep apnea, snoring and/or improving sleep quality. By repositioning the tongue resting spot additional reductions in snoring can be achieved.

Background Art

My previous patents, mentioned above, focused mainly on OSA, or obstructive sleep apnea, although in truth my patented appliances may be used for a variety of purposes where a mouthpiece may be beneficial, including reducing snoring, reducing bruxism, reducing temporomandibular disorder (TMD), clear aligners for teeth straightening, and increasing safety as sports mouth guards. The present application focuses mainly on reduction of snoring and/or improving sleep quality.

There are of course many known oral appliances that claim to reduce or eliminate snoring. Tongue retaining appliances prevent the collapse of the tongue and soft tissues and act to keep the airways open by either a suction bulb feature that is worn similar to an infant pacifier, or have a physical tongue-restraining component, such as a transverse strap that connects the lower left and right molars. Mandibular repositioning appliances support the lower jaw in a position that helps maintain open airways. As I explained in my previous patents, these latter oral appliances are sometimes referred to as mandibular splints. The present disclosure involves the oral appliance or mandibular splint category and features a unique area of thickness added to the palate to reposition the tongue resting spot from the roof to the mouth to the open space of the oral cavity. To compensate for the lowering of the mandible and restoring the proper tongue posture while sleeping.

It has just recently come to my attention that some users, when wearing my oral appliance known under the trade designation DS8™ (available exclusively from Slow Wave™, Inc.), cannot maintain their tongue in the gap created in the front of the appliance. The gap allows the tongue to move forward and out of the airway. What they need is a tongue resting spot to compensate for the lowering of the mandible and restoring the proper tongue posture while sleeping, but without any transverse bands that might cause choking or gagging. US20160135922 discloses "a universal appliance to be inserted in the mouth, which would also be adapted to re-educate the tongue position", however, the document teaches repositioning the tongue by use of a ring which surrounds the tongue and is joined to various structural and functional surfaces. The shaped surfaces in the above patent are used to "re-educate the tongue position", however there is no teaching or suggestion of an area that introduces a tongue resting spot to compensate for the lowering of the mandible and restoring the proper tongue posture while sleeping. U.S. Pat. No. 6,634,353 discloses a method of treating apnea in a patient having sleep apnea and a malocclusion between the maxilla and the mandible. However, this patent does not disclose an oral appliance that has an area that introduces a tongue resting spot to compensate for the lowering of the mandible and restoring the proper tongue posture while sleeping. The method disclosed is for curing malocclusion (lack of occlusion) and includes measuring steps and determining a centering position of the malocclusion and includes use of rubber bands or other biasing means. U.S. Pat. No. 9,585,785 (Hofmann), discloses an "occlusion splint arrangement", featuring "fins" having centering pins and recesses, as seen in the figures of the patent. However, this patent does not disclose an oral appliance including features that has an area that introduces a tongue resting spot to compensate for the lowering of the mandible and restoring the proper tongue posture while sleeping.

Many of the known oral appliances meant to reduce snoring are uncomfortable and/or complicated, leading to reduced use, or non-use. Furthermore, their use in humans may reduce speaking substantially, or at least the ability to speak understandably. In my previous patents I described upper and lower trays that fit over the inside and outside surfaces of a user's upper and lower dentition, respectively, and certain embodiments include left and right ramps designed to move the mandible (lower jaw) downward as it moves backward toward a user's throat.

In light of the above problems, and no apparent solutions available to oral appliance users, I have designed several oral appliances that feature a unique area of thickness added to the palate to reposition the tongue resting spot from the roof to the mouth to the open space of the oral cavity, to compensate for the lowering of the mandible and restoring the proper tongue posture while sleeping.

SUMMARY

In accordance with the present disclosure, oral appliances, apparatus and kits are presented, as well as methods of using same, which reduce or overcome snoring, and which may benefit those suffering from obstructive sleep apnea, and other loss of sleep issues, and/or nasal drainage.

A first aspect of the disclosure is an oral appliance or apparatus (the words "apparatus" and "oral appliance" are used interchangeably herein) having an upper generally arched-shaped member and a lower generally arched-shaped member, comprising:

a) the upper generally arched-shaped member is configured to fit adjacent at least a portion of interior and exterior surfaces of a user's upper dentition, the upper generally arched-shaped member comprising a palate extension that extends posteriorly from the portion configured to fit adjacent the interior surface of the user's upper dentition in an area proximate at least a user's upper central (or central and lateral) incisors to an arcuate distal edge of the palate extension, the upper generally arched-shaped member consisting of a moldable polymeric material;

b) the lower generally arched-shaped member consists of the same moldable polymeric material that is configured to fit adjacent at least a portion of interior and exterior surfaces of the user's lower dentition;

c) the lower generally arch-shaped member comprises a lower right molar and pre-molar extension and a lower left molar and pre-molar extension each consisting of the same moldable polymeric material, the lower right and the lower left molar and pre-molar extensions formed integrally with and projecting generally perpendicularly away from the lower generally arch-shaped member and generally toward the upper generally arch-shaped member, and each having a height that increases uniformly from respective right and left lower posterior molars to anterior pre-molars;

d) the upper generally arch-shaped member comprises an upper right molar and pre-molar extension and an upper left molar and pre-molar extension consisting of the same moldable polymeric material, the upper right and upper left molar and pre-molar extensions formed integrally with and projecting generally perpendicularly away from the upper generally arch-shaped member and generally toward the lower generally arch-shaped member, and each having a second height that is constant from respective right and left upper posterior molars to anterior pre-molars;

e) so that when the user bites or clenches, the upper right molar and pre-molar extension impinges on the lower right molar and pre-molar extension, and the upper left molar and pre-molar extension impinges on the lower left molar and pre-molar extension;

f) the upper and lower generally arch-shaped members having an anterior shape to form a gap ranging from about 1 to about 20 mm, or from about 6 to about 10 mm, and sufficient for at least a portion of the user's tongue to extend forward into the gap without being impeded in forward movement by the apparatus;

g) the lower right molar and pre-molar extension, lower left molar and pre-molar extension, upper right molar and pre-molar extension, and upper left molar and pre-molar extension each configured such that, when the oral appliance is in the user's mouth, the molar and pre-molar extensions create a tendency to keep the user's airway open by maintaining the gap.

A second aspect of the disclosure are methods of making oral appliances of the present disclosure, one method comprising:

scanning a user's upper and lower dentitions and mouth cavity employing a laser scanning appliance to produce a pointcloud image thereof;

uploading the pointcloud image to a computer having one or more dental design software loaded thereon and producing a software version of the oral appliance from the pointcloud image;

uploading the software version of the oral appliance to a 3D printer;

3D printing the upper generally arched-shaped member of the first aspect;

3D printing the lower generally arched-shaped member of the first aspect;

wherein the 3D printing of the lower right molar and pre-molar extension, the lower left molar and pre-molar extension, the upper right molar and pre-molar extension, and the upper left molar and pre-molar extension comprises 3D printing the palate extension.

Another aspect of this disclosure are methods of using the oral appliances, one method comprising:

a) inserting at least one or both of the upper and lower generally arch-shaped members of the first aspect into the user's mouth and fitting the upper generally arch-shaped member adjacent at least the portion of the interior and exterior surfaces of the user's upper dentition, fitting the palate extension against an anterior portion of the user's palate, and fitting the lower generally arch-shaped member adjacent at least the portion of the interior and exterior surfaces of the lower dentition; and b) the user wearing the upper and the lower generally arch-shaped members.

Certain methods may comprise adjusting one or more of:

the upper generally arch-shaped member to fit adjacent at least the portion of the interior and exterior surfaces of the user's upper dentition, adjusting the lower generally arch-shaped member to fit adjacent at least the portion of the interior and exterior surfaces of user's lower dentition, adjusting the palate extension to fit adjacent at least the anterior portion of the user's palate; and combinations thereof.

Another aspect of this disclosure are kits comprising the upper and lower generally arch-shaped members of the first aspect.

In certain embodiments the palate extension extends adjacent a user's palate a length of at least 5 mm measured from the central incisors, or a length of at least 10 mm, or a length of at least 20 mm. In certain embodiments the palate extension has a constant uniform thickness. In certain embodiments the palate extension arcuate distal edge extends laterally left and right from a central longitudinal axis of the upper generally arched-shaped member at least to respective left and right first premolars, and in certain embodiments at least to respective left and right second premolars. In certain embodiments the height of each of the lower right and the lower left molar extensions that increases uniformly from respective right and left lower posterior molars to respective right and left lower anterior molars increases from about 2 mm to about 10 mm.

In certain embodiments the lower and the upper generally arch-shaped members are "full members", meaning that the upper generally arch-shaped member covers and fits over a user's entire upper dentition, and the lower generally arch-shaped member fits over a user's entire lower dentition. Stated differently, "full members" means that every cross-section of the upper generally arch-shaped member is U-shaped, while every cross-section of the lower generally arch-shaped members is an inverted U-shape. In other embodiments, the lower and the upper generally arch-shaped members are both lacking frontal vestibular bands in the areas in front of the incisors and the canines, while one upper palatal band connects left and right pre-molar and molar trays adjacent and behind the upper incisors and canines, and a similar lower palatal band connects left and right pre-molar and molar trays adjacent and behind the lower incisors and canines. In other embodiments, the lower and the upper generally arch-shaped members both cover the molars, premolars, canines, and lateral incisors but not the central incisors, effectively leaving four teeth (two maxillary central incisors and two mandibular central incisors) uncovered by either of the generally arch-shaped members, but having two palatal bands, one connecting the upper left and upper right generally arch-shaped members, and the other connecting the lower left and lower right generally arch-shaped members, but lacking any vestibular bands. In other embodiments, the lower and the upper generally arch-shaped members both cover the molars, premolars, and canines, but not the lateral or central incisors, effectively leaving eight teeth (four maxillary incisors and four mandibular incisors) uncovered by either of the generally arch-shaped members, but having two palatal bands, one connecting the upper left and upper right generally arch-shaped members, and the other connecting the lower left and lower right generally arch-shaped members, but lacking any vestibular bands.

In certain embodiments the moldable or printable biocompatible polymeric material may be selected from the group consisting of synthetic and natural materials. As used herein "moldable" includes polymeric materials that nay be shaped by heat and molding. As used herein "printable" is intended to include additive manufacturing processes as described herein, and wherein either the end polymer itself is printable, or its precursor resins are printable and that may be later cured or otherwise solidified, for example by light having wavelengths in the UV light ranges or IR light (heat) ranges or other wavelengths, depending on the resin. In certain embodiments the moldable or printable biocompatible polymeric material may be selected from the group consisting of polyurethanes, polysulfones, polycarboxylates, perfluorinated polymers, polyacrylics, polyvinyls, polyvinyl alcohols, silicones, polyolefins, and blends and copolymers thereof. In certain embodiments the moldable or printable biocompatible polymeric material may be selected from a durable fade-resistant acrylic that retains its shape and color for at least four years, and a very pliable, soft, custom-injected silicone.

In certain embodiments, the upper and lower generally arched-shaped members each consist essentially of an identical moldable or printable, biocompatible polymeric material. Any of the oral appliances or apparatus described herein may be part of a kit comprising one or both upper and lower generally arch-shaped members substantially as described herein, in certain embodiments packaged in a carrying case.

Further aspects and advantages of apparatus and methods of the present disclosure will become apparent by reviewing the detailed description that follows.

Figure 1:
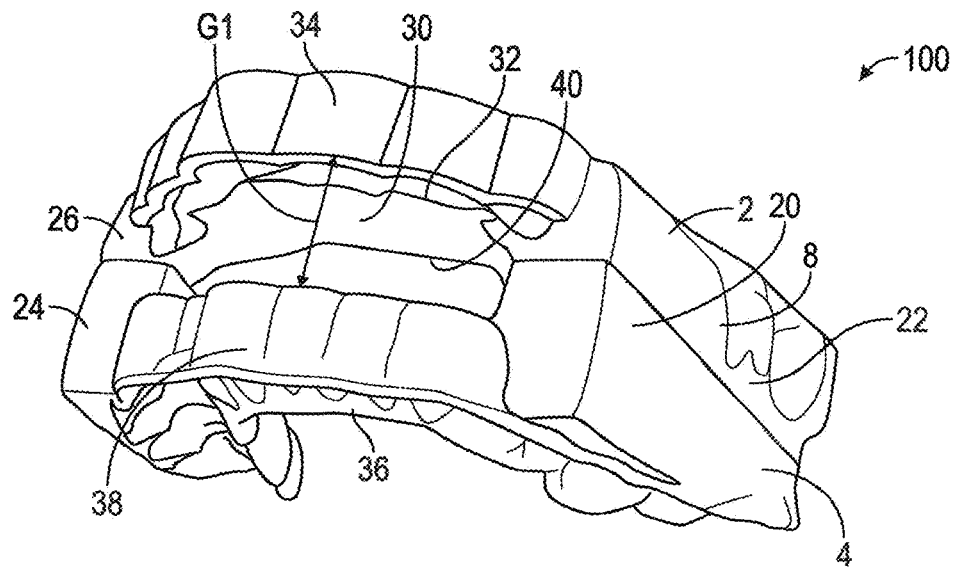
FIGS. 1, 2, and 14 are perspective schematic illustrative views of one apparatus or kit embodiment within the present disclosure, viewed from the lower left, the lower right, and lower central, respectively.

It is to be noted, however, that the appended drawings are not to scale and illustrate only typical embodiments of this disclosure and are therefore not to be considered limiting of its scope, for the apparatus, kits, and methods of the disclosure may admit to other equally effective embodiments. Identical reference numerals are used throughout the several views for like or similar elements.

DETAILED DESCRIPTION

In the following description, numerous details are set forth to provide an understanding of the disclosed oral appliances, kits and methods of their use. However, it will be understood by those skilled in the art that the oral appliances, kits, and methods covered by the claims may be practiced without these details and that numerous variations or modifications from the specifically described embodiments may be possible and are deemed within the claims. For example, wherever the term "comprising" is used, embodiments and/or components where "consisting essentially of" and "consisting of" are also explicitly disclosed herein and are part of this disclosure. An example of "consisting essentially of" may be with respect to the composition of a generally arch-shaped member: a generally arch-shaped member consisting essentially of a biocompatible polymer means there may be a minor portions or trace amounts of organic and/or inorganic chemical species, such monomers and other polymer precursors, noble metals such as platinum, and the like. An example of "consisting of" may be an oral appliance made up of components that are one or more biocompatible polymers and no or substantially no other chemical species. An example of "consisting essentially of" may be with respect to a particular palate extension that consists essentially of a biocompatible polymer, meaning that a minor portion, perhaps up to 10, or up to 5, or up to 4, or up to 3, or up to 2, or up to 1 wt. percent may be metal, such as metal wire or other sub-component that helps in positioning the palate extension against the user's palate. An example of oral appliances using the transition phrase "consisting of" includes those where an appliance has only molar and premolar trays, with one band connecting the upper left and right trays behind the upper canines and incisors, a second band connecting the upper left and right trays in front of the upper canines and incisors, a third band connecting the lower left and right trays behind the lower canines and incisors, and a fourth band connecting the lower left and right trays in front of the lower canine and incisors, with molar and premolar extensions on each tray. The term "comprising" and derivatives thereof is not intended to exclude the presence of any additional component, step or procedure, whether or not the same is disclosed herein. In order to avoid any doubt, all compositions, apparatus, systems, and methods claimed herein through use of the term "comprising" may include any additional component, step, or procedure unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination. Unless stated to the contrary, implicit from the context, or customary in the art, all parts and percentages are based on weight and all test methods are current as of the filing date hereof. The acronym "ASTM" means ASTM International, 100 Barr Harbor Drive, PO Box C700, West Conshohocken, PA, 19428-2959 USA.

All numbers, including degree angles, disclosed herein are approximate values, regardless of whether the word "about" or "approximate" is used in connection therewith. They may vary by 1%, 2%, 5%, and sometimes, 10 to 20%. Whenever a numerical range with a lower limit, RL and an upper limit, RU, is disclosed, any number falling within the range is specifically disclosed. In particular, the following numbers within the range are specifically disclosed: R=RL+ k*(RU−RL), wherein k is a variable ranging from 1% to 100% with a 1% increment, i.e., k is 1%, 2%, 3%, 4%, 5%, . . . , 50%, 51%, 52%, . . . , 95%, 96%, 97%, 98%, 99%, or 100%. Moreover, any numerical range defined by two R numbers as defined in the above is also specifically disclosed. All percentages herein are based on weight unless otherwise specified. All U.S. and non-U.S. patent applications and U.S. and non-U.S. Patents referenced herein, and their priority documents, are hereby explicitly incorporated herein by reference. In the event definitions of terms in the referenced patents and applications conflict with how those terms are defined in the present application, the definitions for those terms that are provided in the present application shall be deemed controlling.

As used herein the phrase "generally arched-shaped" means the shape of a member resembles an arch in the same way that the upper and lower teeth of a user resemble arches. The phrase "adjacent at least a portion of interior and exterior surfaces", as that term is used herein when referring to the "upper and lower generally arched-shaped members configured to fit adjacent at least a portion of interior and exterior surfaces of a user's upper and lower dentitions", means that these members are adjacent to and touching at least one surface of the upper or lower teeth concerned, but some "looseness" is allowed, so that the members may move away from the teeth slightly, for example if the material of the member stretches or deforms, such as during insertion into or removal from the mouth. In certain embodiments "adjacent" in this context means a separation of from about 0.05 to about 0.5 mm, or from about 0.1 to about 0.3 mm. The term "molar extension" is meant to convey general location and does not mean that the extensions are always precisely covering all molars and premolars in those locations; in other words, they are meant to be relative terms, such as front, anterior, back, posterior, upper and lower, and the like, are relative terms. "Canines" or "canine" location is generally between lower (mandibular) premolars and lower incisors, and between upper premolars and upper incisors; "molars" is used herein to include premolars. As used herein the term "user" means a human or other mammal that employs an apparatus of this disclosure in its mouth. The term "subject" may also be used and is considered interchangeable with the term "user."

The present disclosure relates generally to apparatus, kits, and methods for reducing or eliminating snoring, although they may also be beneficial for reducing or eliminating sleep disorders and other disorders, such as obstructive sleep apnea (OSA) and/or nasal drainage. A particular use for apparatus and kits of this disclosure is for humans, but they may also be used for other mammals. Certain embodiments may also be used as athletic mouth guards for upper, lower, or both dentitions.

In certain embodiments the upper and lower members each may comprise a moldable material selected from the group consisting of synthetic and natural materials. Synthetic materials may be selected from the group consisting of polymeric materials, as further discussed herein. In certain apparatus the arch-shaped members, molar extensions, and palate extensions may comprise the same or different polymeric materials. In certain embodiments, the polymeric material may be a light-curable polymer-based resin designed for the fabrication of biocompatible, long-term use, removable dental and orthodontic appliances by additive manufacturing that is known under the trade designation Dental LT Clear V2, available commercially from Formlabs, Millbury, Ohio (USA). Material mechanical properties are provided in Table 1. As noted by the supplier, material properties may vary based on part geometry, print orientation, print settings, temperature, and disinfection or sterilization methods used.

TABLE 1

Mechanical Properties of light-curable polymer-based resin known under the trade designation "Dental LT Clear V2"

| Mechanical Properties | Post Cured Results | Method |
| --- | --- | --- |
| Ultimate Tensile Strength | ≥50 MPa | ASTM D638 |
| Flexural Modulus | ≥2000 MPa | ASTM D790 |
| Elongation | ≥10% | ASTM D638 |

Referring now to the drawing figures, FIGS. 1, 2, 8, and 14 are perspective schematic illustrative views of one apparatus or kit embodiment 100 within the present disclosure, viewed from the lower left, the lower right, and lower central viewpoints, respectively. Apparatus or kit embodiment 100 includes an upper generally arch-shaped member 2 and a lower generally arch-shaped member 4. Upper generally arch-shaped member 2 includes an exterior molar wall 8 and an interior molar wall 10 (better seen in FIG. 8, for example), custom-shaped for the user's upper molar and premolar dentition, and which together define a molar trough 6 for friction fitting adjacent the upper molar and premolar dentition of a user. (As the left and right are basically the same, for brevity these are not called out in the drawing.) An upper connecting portion 12 (FIG. 9) connects exterior wall 8 and interior wall 10. Connecting portion 12 is rather flat or planar exterior in the area of the premolars and molars and assumes an interior shape of the surface of the user's molars and premolars. Similarly, lower generally arch-shaped member 4 includes an exterior wall 14, and an interior wall 16 in the area of lower molars and premolars. A lower connecting portion 18 connects walls 14 and 16, and as with upper connecting portion 12, lower connecting portion 18 has a planar exterior surface near the lower molars and premolars of the user and an interior surface that assumes the shape of the surfaces of the user's lower molars and premolars.

Embodiment 100 includes a lower left, generally wedge-shaped molar and premolar extension 20 and a generally flat upper left molar and premolar extension 22, each extending generally perpendicularly away from their respective members. Similarly, embodiment 100 includes a lower right, generally wedge-shaped molar and premolar extension 24 and a generally flat upper right molar and premolar extension 26, each extending generally perpendicularly away from their respective members. These wedges or ramps help maintain the device's vertical opening "G1" (FIG. 1) they have an anterior height of about 20 mm and decreases to about 2 mm in the posterior. The length of the upper and lower molar extensions, i.e., the distance from the posterior terminus to the anterior terminus of a given molar extension, may be 10 mm or more, or may range from 10 to about 50 mm or from about 12 to about 24 mm.

Figure 2:
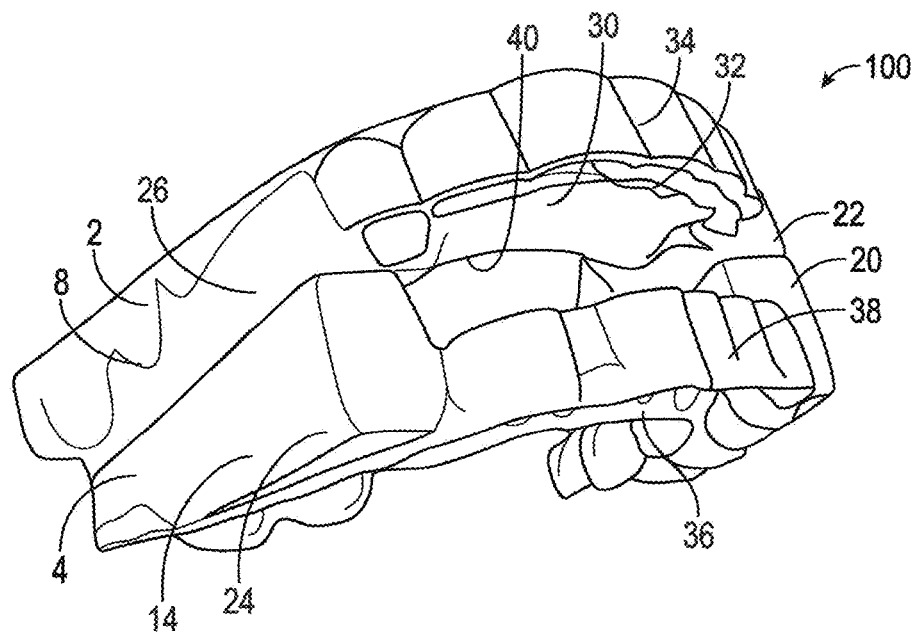
Figure 16:
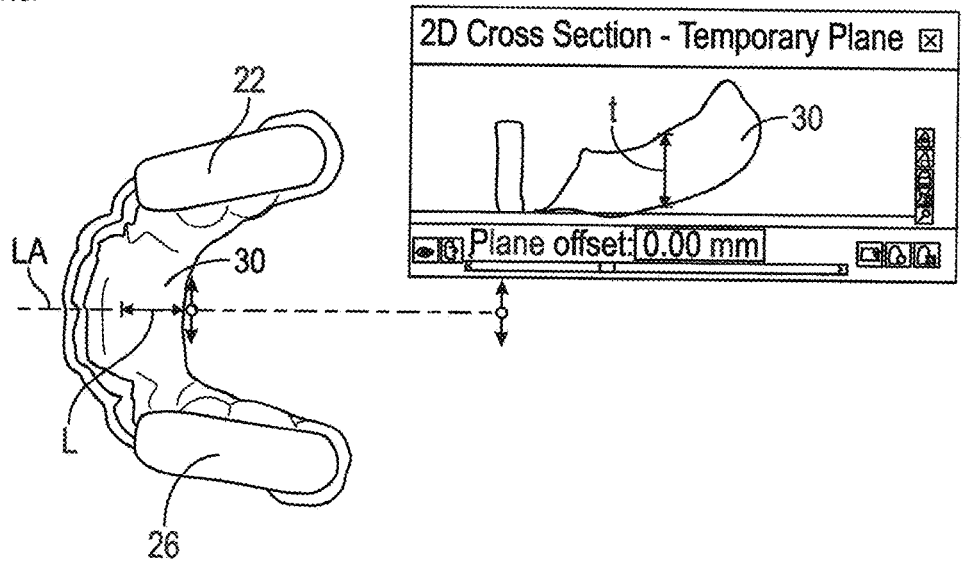

Referring to FIGS. 1 and 2, as well as FIGS. 8, 9, 11, 13, 14, and 16, an important feature of apparatus and kits of the present disclosure is the presence of a palate extension 30 that extends generally posteriorly along the roof or palate of a user from a mold portion 32 that fits snuggly adjacent the rear of the upper incisors and canines of a user. Another mold portion 34 fits snuggly adjacent a front surface of the user's upper incisors and canines. Mold portions 32, 34, connect on their ends to front terminus points of upper molar extensions 22, 26, as best illustrated in FIGS. 1, 2, 9, and 11. A mold portion 36 fits snuggly adjacent the rear of the lower incisors and canines of a user, and another mold portion 38 fits snuggly adjacent a front surface of the user's lower incisors and canines. Mold portions 36, 38, connect on their ends to front terminus points of lower molar extensions 20, 24, as best illustrated in FIGS. 1, 2, 10, and 12. As best illustrated in FIGS. 9, 11, 13, 14, and 16, palate extension 30 has an arcuate edge 40 that extends a length "L" away from upper mold portion 32, and curves toward and connects with inner walls 10 of the upper tray 2, and has a thickness "t" as illustrated in FIG. 16. Length L (at the position indicated in FIGS. 9, 11, and 16) extends from the maxillary incisal edge to the palate and may range from about 2 to about 20 mm, or from about 4 to about 18 mm, or from about 6 to about 16 mm. Thickness t (at the position indicated in FIG. 16) may range from about 2 mm to about 8 mm, or from about 3 to about 7 mm, or from about 4 to about 6 mm, and may be slightly more or less at positions away from the position indicated in FIG. 16, depending on the user.

Figure 3:
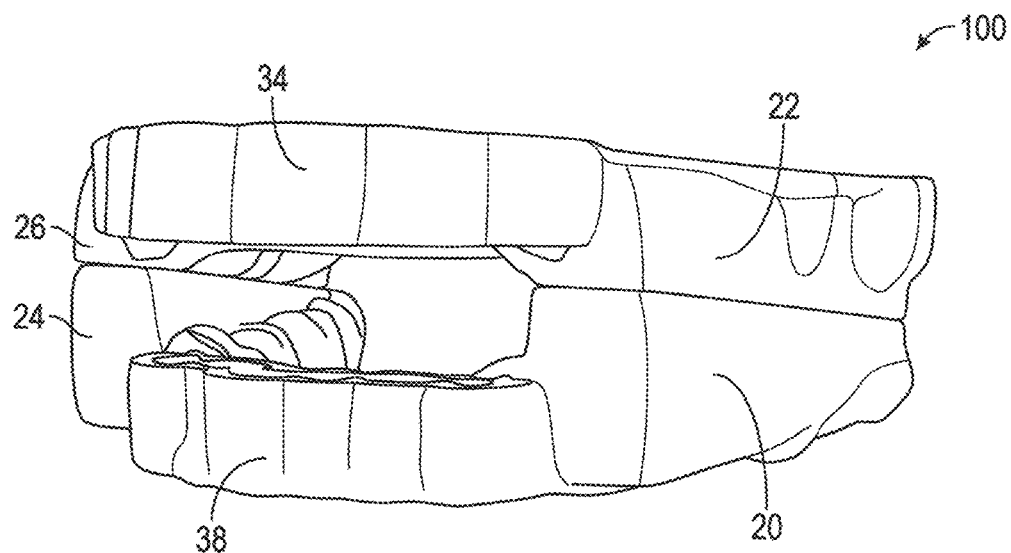
FIGS. 3 and 4 are schematic illustrative front elevation views of the apparatus or kit embodiment illustrated in FIGS. 1 and 2, with FIG. 3 being a view taken from the left of center, and FIG. 4 being a view taken from the right of center.
Figure 4:
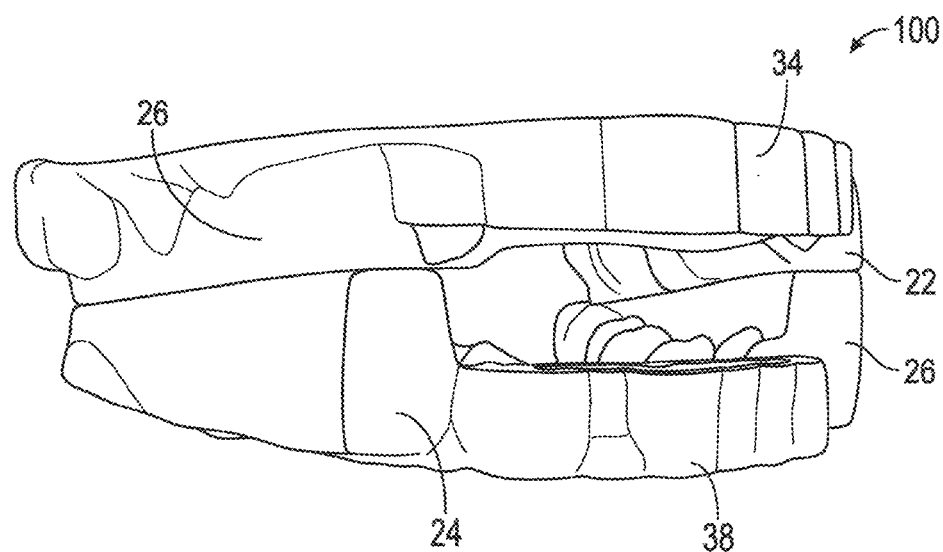
Figure 5:
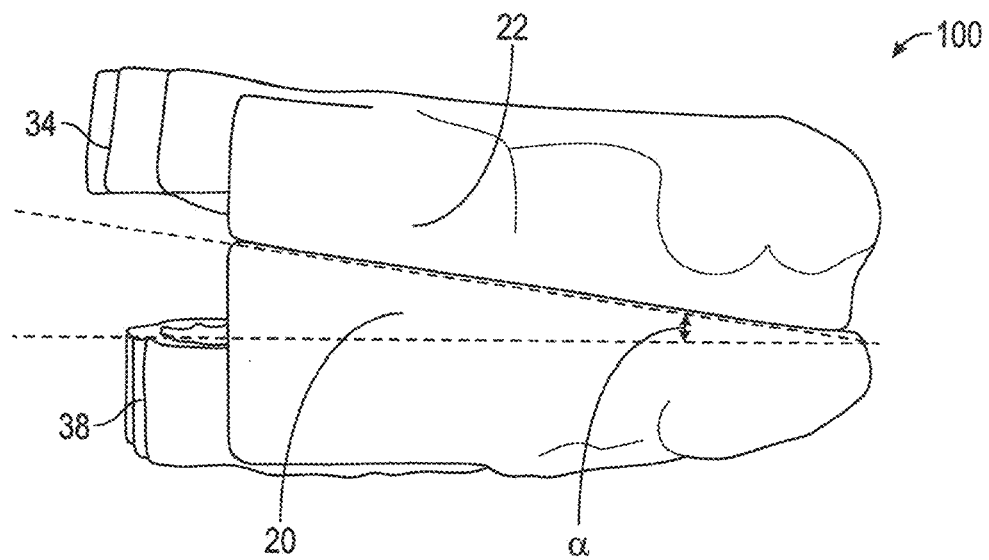
FIGS. 5 and 6 are left-side and right-side schematic illustrative elevation views of the apparatus or kit embodiment of FIGS. 1-4.
Figure 6:
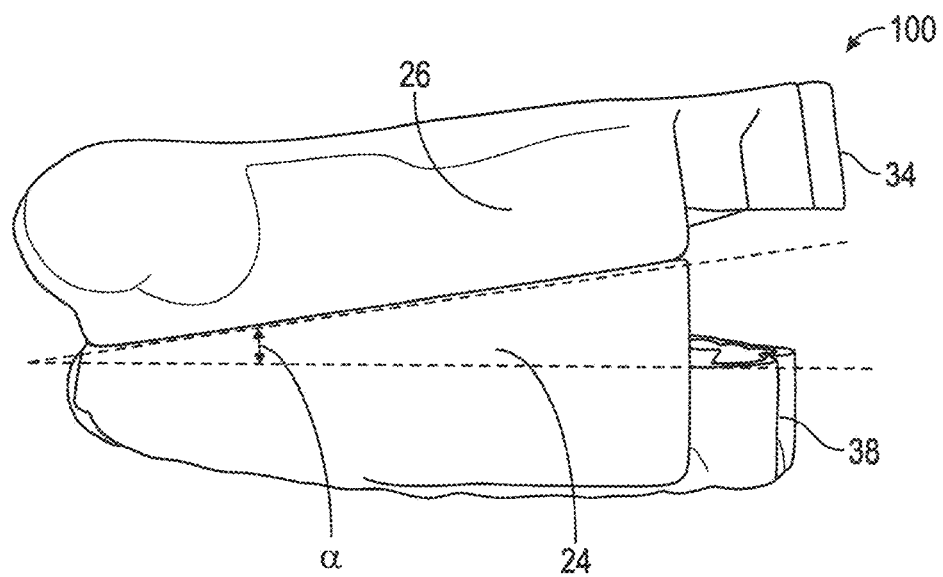
Figure 7:
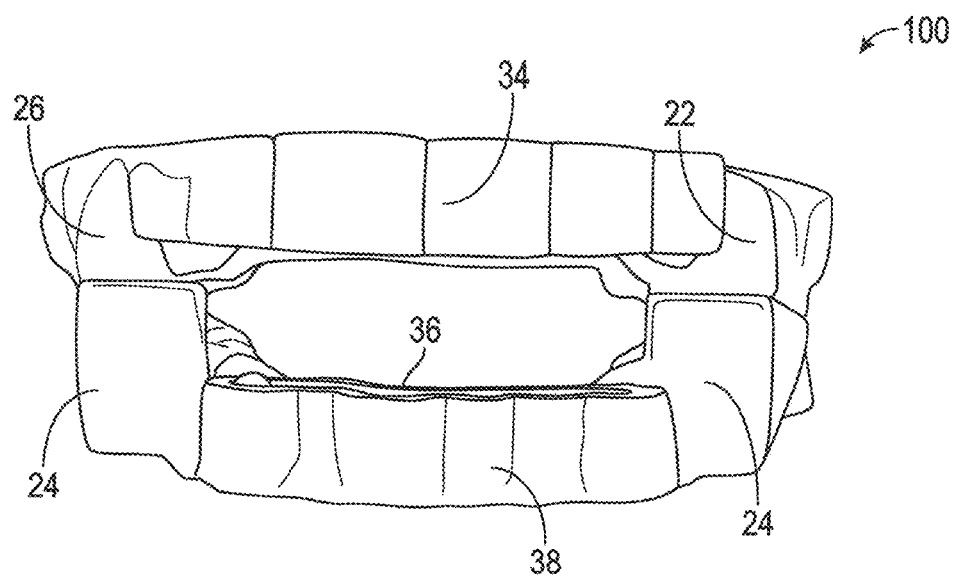
FIGS. 7 and 8 are front and rear schematic illustrative elevation views of the embodiment illustrated in FIGS. 1-6.
Figure 8:
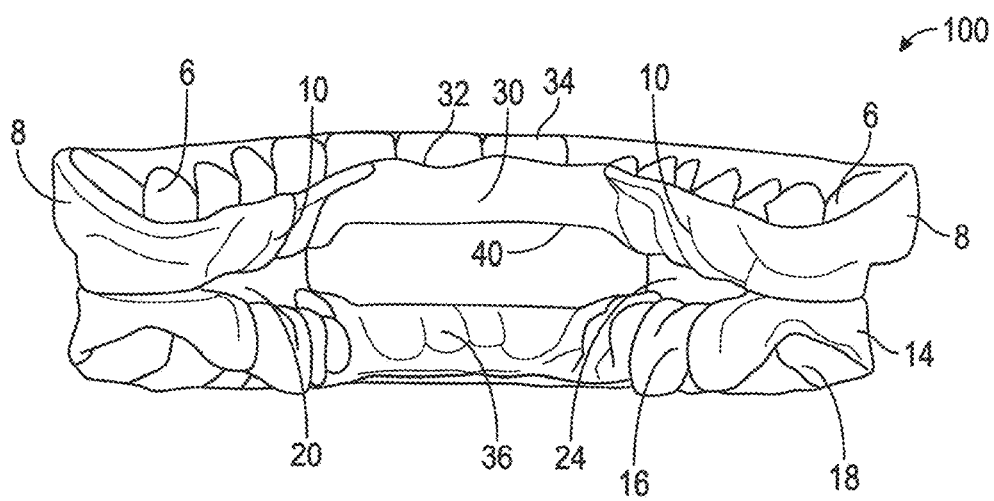
Figure 11:
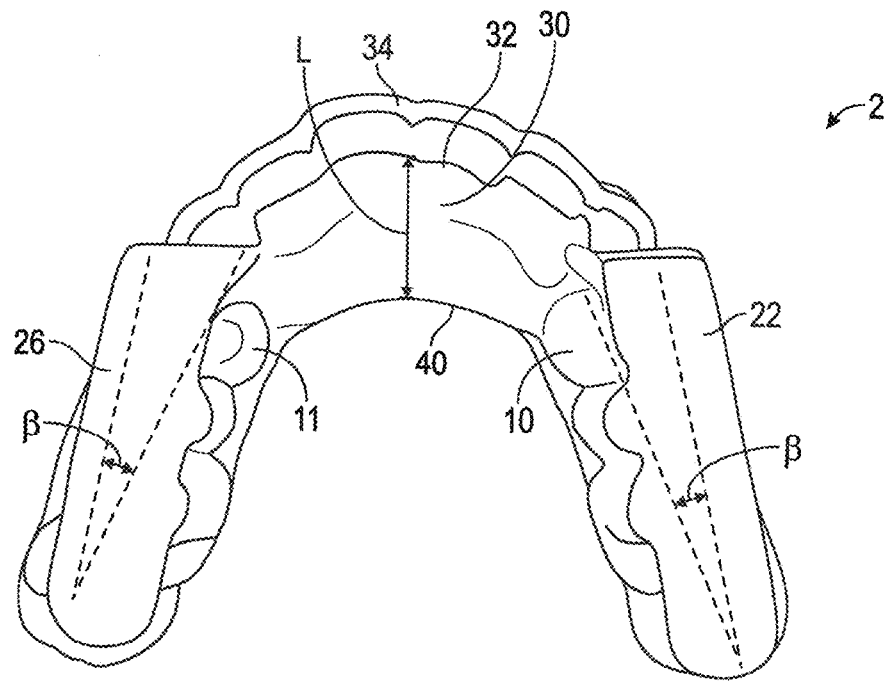
FIGS. 11 and 12 are reverse plan and plan schematic illustrative views, respectively, of the upper tray and lower tray of the embodiment illustrated in FIGS. 1-10.
Figure 12:
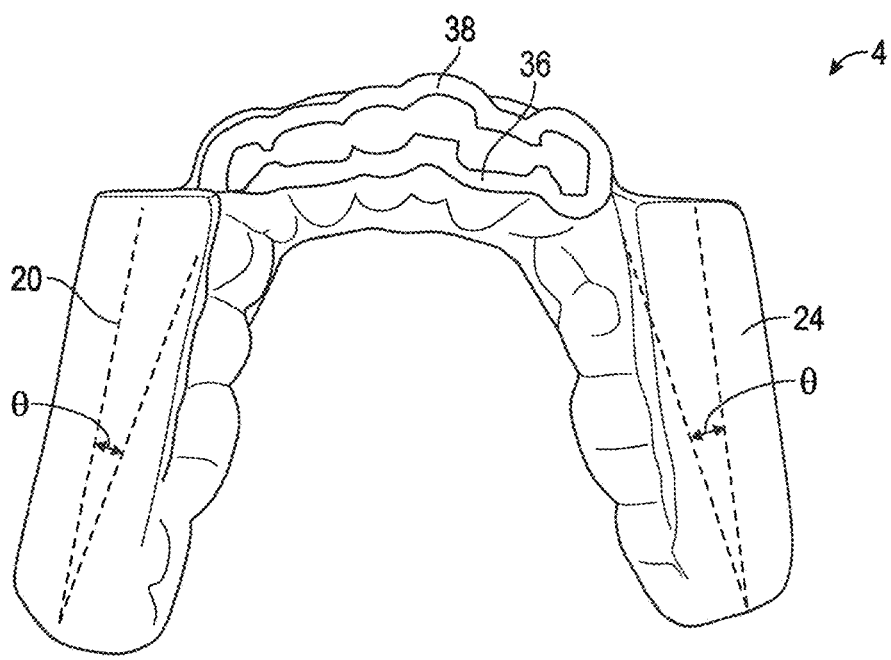

FIGS. 3 and 4 are schematic illustrative front elevation views of apparatus or kit embodiment 100 illustrated schematically in FIGS. 1 and 2, with FIG. 3 being a view taken from the left of center, and FIG. 4 being a view taken from the right of center. FIGS. 5 and 6 are left-side and right-side schematic illustrative elevation views of apparatus or kit embodiment 100 illustrated schematically in FIGS. 1-4, where attention is drawn to angle "a" between mating surfaces of lower left, generally wedge-shaped molar and premolar extension 20 and generally flat upper left molar and premolar extension 22, and between mating surfaces of lower right, generally wedge-shaped molar and premolar extension 24 and generally flat upper right molar and premolar extension 26. Angle "$\alpha$" may range from about 5 to about 25 degrees, or from about 10 to about 20 degrees. FIG. 7, in conjunction with FIGS. 11 and 12, illustrate schematically angles "$\beta$" and "$\theta$", which in most embodiments are the same, but can be different, which are angles that members 20, 22, 24, and 26 make with their respective molar troughs 6, 18 (FIG. 8) for friction fitting adjacent the upper and lower molar and premolar dentition of a user. Members 20, 22, 24, and 26 are angled outwardly from posterior to anterior positions in order to provide the user's tongue more room, as discussed in my U.S. Pat. No. 11,813,192. FIGS. 7 and 8 are front and rear schematic illustrative elevation views of embodiment 100 illustrated schematically in FIGS. 1-6.

Figure 9:
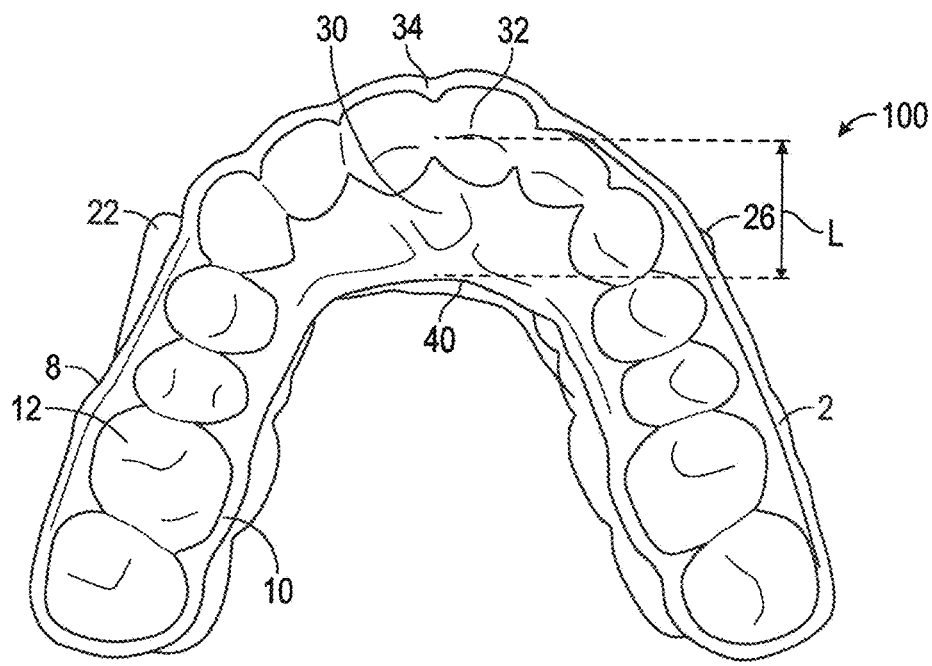
FIGS. 9 and 10 are plan and reverse plan schematic illustrative views, respectively, of the embodiment illustrated in FIGS. 1-8.
Figure 10:
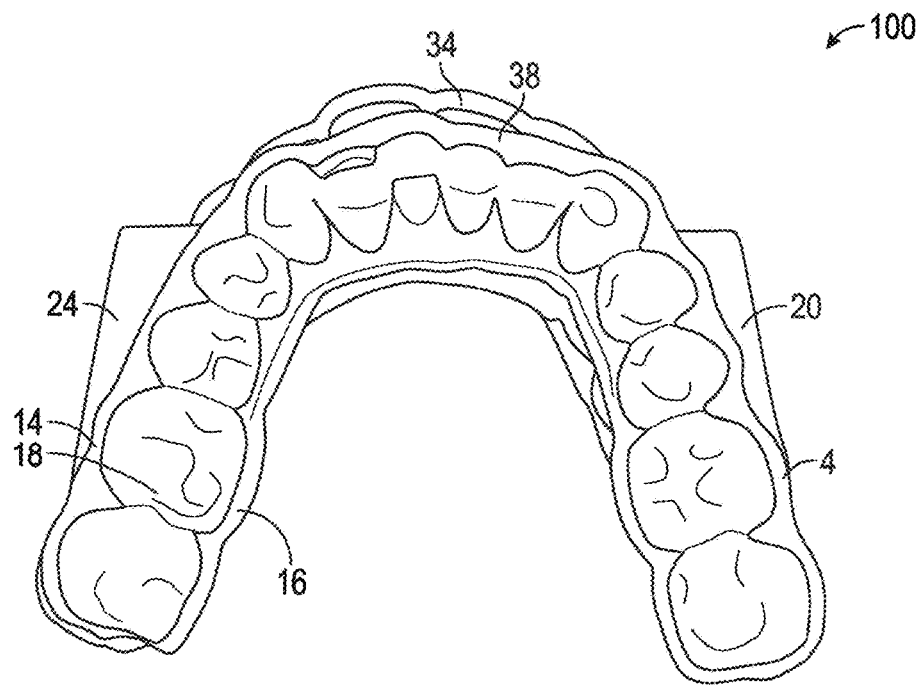
Figure 13:
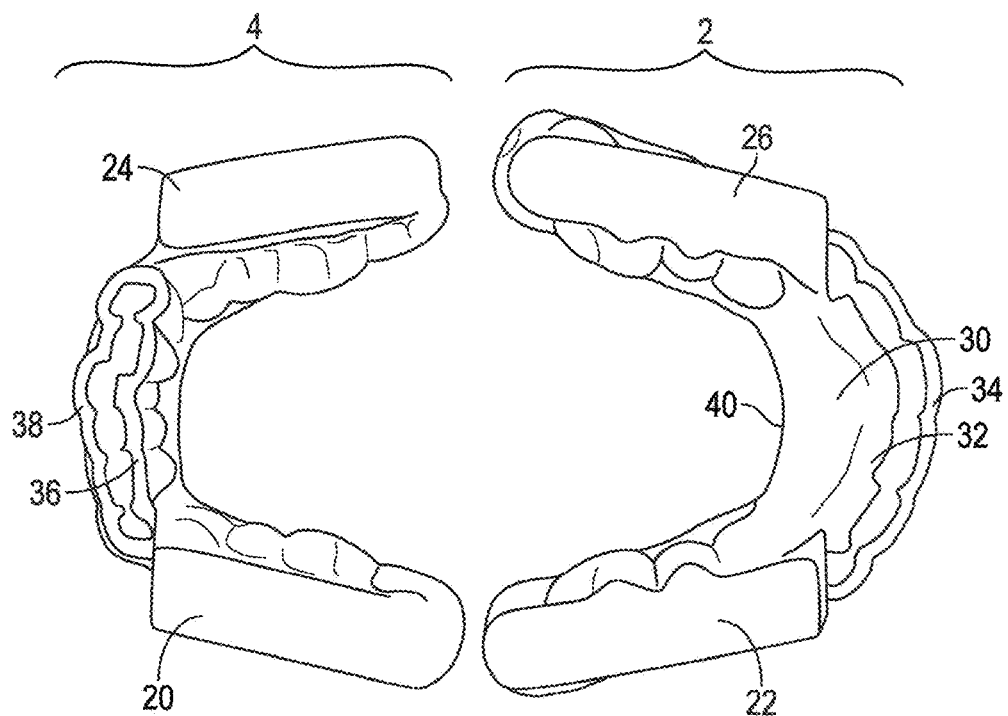
FIG. 13 is an exploded schematic view of the embodiment illustrated in FIGS. 1-10.
Figure 14:
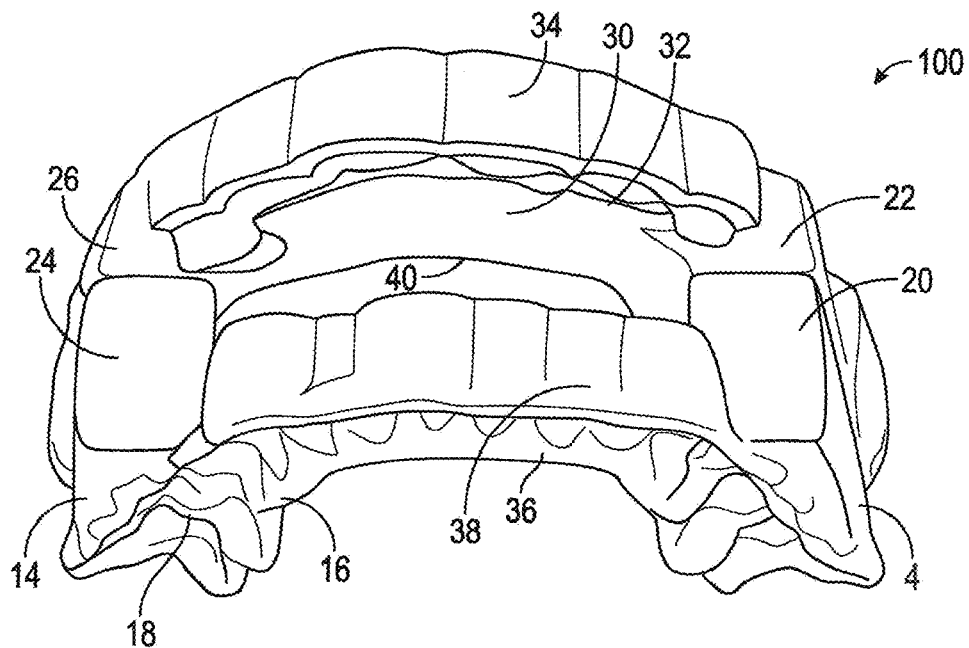

FIGS. 9 and 10 are plan and reverse plan schematic illustrative views, respectively, of embodiment 100 illustrated in FIGS. 1-8, while FIGS. 11 and 12 are reverse plan and plan schematic illustrative views, respectively, of the upper tray and lower tray of embodiment 100 illustrated schematically in FIGS. 1-10. FIG. 13 is an exploded schematic view of embodiment 100 illustrated schematically in FIGS. 1-10.

Figure 15:
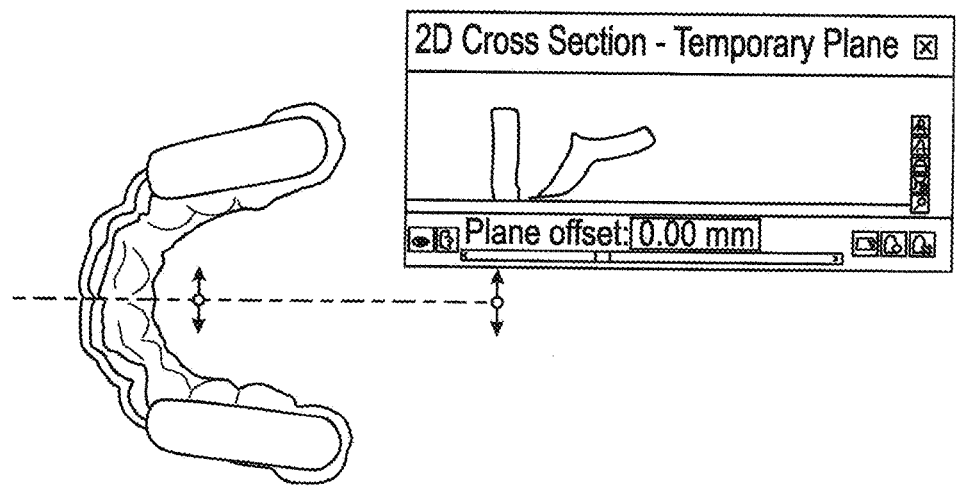
FIGS. 15 and 16 are reverse plan views before and after adding a palate extension to the upper tray.

FIGS. 15 and 16 are reverse plan views before and after adding palate extension 30, with the inset of FIG. 16 illustrating schematically added thickness of palate extension 30.

Upper generally arch-shaped member 2 may comprise, or consist essentially of, or consist of upper left and upper right molar extensions (22, 26) of the same moldable, biocompatible polymeric material formed integrally therewith. Upper molar extensions 22, 26 project generally perpendicularly away from upper full generally arch-shaped member 2 and generally toward respective lower molar extensions 20, 24 of member 4 in mating configuration such that when the user bites, upper right molar extension 26 impinges on lower right molar extension 24 only at the mating surfaces, and upper left molar extension 22 impinges on lower left molar extension 20 only at the mating surfaces.

Extensions 20, 22, 24, and 26 are selected and configured such that, when the apparatus is in a user's mouth, the lower dentition, lower generally arched-shaped member 4, and mandible are not constrained in forward (anterior) or backward (posterior) movement, and allow lower generally arch-shaped member 4, lower dentition and mandible to move downward as a user relaxes, away from the user's throat, tending to keep a user's throat airway open. Furthermore, upper and lower full generally arch-shaped members 2, 4, are configured to form a gap G1 sufficient for at least a portion of the user's tongue to extend forward into the gap without being impeded in forward movement by the apparatus, and without the tongue being constrained, pulled or grabbed in any way. During use, although movement of the lower jaw backwards is a natural movement during sleep, as this occurs, embodiment 100 will tend to train the user's tongue to naturally migrate forward by the user using the tongue tip to search for the palate extension 30 and keep the throat airway open, as well as by creating gap G1 between upper portion 2 and lower portion 4, near the front teeth, as indicated by double-headed arrow G1 in FIG. 1, and partially defined by space between anterior portions of upper and lower molar extensions 20, 22, 24, 26. This gap may be important in methods of reducing nasal drainage, perhaps more important than movement of the lower jaw.

As mentioned previously, FIGS. 11 and 12 illustrate how positioning the molar extensions 20, 22, 24, and 26 at angles $\beta$ and $\theta$ provides more room for a user's tongue as the tongue relaxes. This is accomplished by positioning the molar extensions, as illustrated in FIGS. 11 and 12, at angles $\beta$ and $\theta$ to a generally longitudinal axis of trays 2, 4, in their respective molar regions. Angles and may be the same or different and each may independently range from about 5 degrees to about 30 degrees, or from about 5 to about 25 degrees, or from about 10 to about 25 degrees. Only a few millimeters (about 1 to 5 mm, or about 1 to 3 mm) of extra lateral space for the tongue may be required to have a significant effect on providing more space for the user's airway.

It should be emphasized that features as disclosed in my previous U.S. Patents may be employed, if desired or necessary for some users, in all embodiments of the appliances of the present disclosure. These patents are expressly incorporated herein by reference: U.S. Pat. Nos. 9,144,515; 9,408,743; 9,439,802; 9,445,938; 10,299,957; 11,273,071; 11,779,486; and U.S. Pat. Nos. 11,806,274; and 11,813,192.

The materials of construction of the upper and lower general arch-shaped members, molar and premolar extensions, palate extensions, and other members may comprise any moldable or printable plastic (polymeric) material, or ceramic material, or metallic material, or combination thereof that is approved for use in oral medical appliances and appliances for human use and that may be custom fitted for each user and tooth-retained via friction grip, and materials approved for animal use. The members may comprise a single material, or combination of materials. The members may comprise more than one layer of material, and each layer may be the same or different. The polymeric materials may be filled with various fillers, extenders, pigments, and other additives. In embodiments consisting essentially of moldable, biocompatible polymeric material, these fillers, extenders, pigments, and other additives are present in limited amounts to the extent necessary to substantially exceed minimum safety and effectiveness standards. Suitable polymeric materials include thermoplastics, thermosetting polymers, elastomers, and thermoplastic elastomers. The polymeric materials may comprise co-polymers, terpolymers, and blends of two or more chemical types of polymers, or blends of two or more polymers of the same chemical type, for example, a blend of two thermoplastics having different molecular weights.

Examples of specific polymers, in addition to the light-curable polymer-based resin designed for the fabrication of biocompatible, long-term use, removable dental and orthodontic appliances by additive manufacturing that is known under the trade designation Dental LT Clear V2, include polyacrylics, polyvinyls, polyvinyl alcohols, and the like. An example of a suitable polymeric material is a durable fade-proof acrylic that retains its shape and color for at least four-five years. Another example is made of a very pliable, soft, custom-injected silicone. Another example is a polymeric material compatible with home/office based bleaching techniques, such as the material used to make an OSAP appliance, and materials that can be molded into a ready-made semi-universal trial version, which may be suitable for patients who cannot endure having their impressions taken. In addition, the trial version is an inexpensive way to test a particular patients' tolerance to oral therapy. Another example is the material used in the appliance known under the trade designation SAGA. This appliance consists of a hard acrylic shell laminated to a soft vinyl liner. Another example is the acrylic material (Bruxeze™) that softens in hot water to provide a combination of comfort, strength, and retention, and which is used in the Adjustable PM Positioner™, an appliance that fits over all maxillary and mandibular teeth. Another example are the materials used in the appliance known as SomnoGuard® AP, which consists of an upper and a lower tray each made of two materials. The outer tray shells consist of solid clear and transparent medical grade polycarbonate. The inner lining which accommodates the teeth impressions is made of a thermoplastic copolymer. After the oral appliance is heated in a hot water bath its thermoplastic body molds easily to the teeth and jaws allowing any medical doctor to fit the appliance chair side. Yet another example is the material employed in the appliance known as SomnoGuard AP Pro®, which is a dental lab made two-part mandibular adjustable positioner to treat snoring and mild to moderate sleep apnea, and comprises common acrylic/elastomeric thermoform dental materials available in any dental lab after taking impressions of the lower and upper jaws and producing plaster models. Other polymeric materials that may be useful include nitinol, silicone, a PET, or any other biocompatible polymeric material. Other possible examples include PTFE, e-PTFE, polypropylene, polyurethane, polycarbonate, polyethylene terephthalate, stainless steel, titanium, tantalum, gold, polyvinidylene fluoride and combinations thereof. "Biocompatibility" may be determined in accordance with national and/or international standards, such as ISO 10993.

The molar and premolar extensions may be integrally molded with their respective upper or lower generally arch-shaped members as illustrated schematically in the various figures using special molds, or may be made using additive manufacturing methods, such as 3D printing. In certain embodiments, one or more molding or printing steps may be required to build up the molar extensions, palate extensions, etc., to functional length and height. Also, the methods may include printing steps featuring specific polymers, colors, shapes, software, and the like. 3D printers that may be useful are the 3D printers known under the trade designation Formlabs Form 3B+ and 3BL, available from Formlabs, Millbury, Ohio (USA).

Upper and lower trays, and various components, such as palate extensions, as described herein may be made using a variety of additive and/or subtractive processes, including molding, machining, stamping and like additive processes, and/or subtractive processes such as net-shape casting (or near-net shape casting) using rapid prototype (RP) molds. Net-shape or near-net shape casting methods of making a variety of molds for producing a variety of complex products are summarized in patents assigned to 3D Systems, Inc., Rock Hill, South Carolina, U.S.A., for example U.S. Pat. No. 8,285,411. As summarized in the '411 patent, a number of technologies presently exist for the rapid creation of models, prototypes, and objects for limited run manufacturing. These technologies are generally called Solid Freeform Fabrication ("SFF") techniques. Some SFF techniques include stereolithography, selective deposition modeling, laminated object manufacturing, selective phase area deposition, multi-phase jet solidification, ballistic particle manufacturing, fused deposition modeling, particle deposition, laser sintering, film transfer imaging, and the like. Generally, in SFF, complex parts are produced from a build material in an additive fashion as opposed to conventional fabrication techniques, which are generally subtractive in nature. For example, in most conventional subtractive fabrication techniques material is removed by machining operations or shaped in a die or mold to near net shape and then trimmed. In contrast, additive fabrication techniques incrementally add portions of a build material to targeted locations, layer by layer, in order to build a complex part. SFF technologies typically utilize a computer graphic representation of a part and a supply of a build material to fabricate the part in successive layers. According to the '411 patent, SFF technologies may dramatically shorten the time to develop prototype parts, can produce limited numbers of parts in rapid manufacturing methods, and may eliminate the need for complex tooling and machining associated with conventional subtractive manufacturing methods, including the need to create molds for custom applications. In addition, customized parts can be directly produced from computer graphic data (e.g., computer-aided design (CAD) files) in SFF techniques. Generally, in most techniques of SFF, structures are formed in a layer by layer manner by solidifying or curing successive layers of a build material. For example, in stereolithography a tightly focused beam of energy, typically in the ultraviolet radiation band, is scanned across sequential layers of a liquid photopolymer resin to selectively cure resin of each layer to form a multilayered part. In selective laser sintering, a tightly focused beam of energy, such as a laser beam, is scanned across sequential layers of powder material to selectively sinter or melt powder (such as a metal or ceramic powder) in each layer to form a multilayered part. In selective deposition modeling, a build material is jetted or dropped in discrete droplets, or extruded through a nozzle, such that the build material becomes relatively rigid upon a change in temperature and/or exposure to actinic radiation in order to build up a three-dimensional part in a layerwise fashion. In another technique, film transfer imaging ("FTI"), a film transfers a thin coat of resin to an image plane area where portions of the resin corresponding to the cross-sectional layer of the part are selectively cured with actinic radiation to form one layer of a multilayer part. Certain SFF techniques require the part be suspended from a supporting surface such as a build pad, a platform, or the like using supports that join the part to the supporting surface. Prior art methods for generating supports are described in U.S. Pat. Nos. 5,595,703; 6,558,606; and 6,797,351. The Internet website of Quickparts-.com, Inc., Atlanta, GA, a subsidiary of 3D Systems Inc., has more information on some of these techniques and materials that may be used.

Methods of making an oral appliance of the present disclosure using additive manufacturing may comprises scanning a user's upper and lower dentitions and mouth cavity employing a laser scanning appliance to produce a pointcloud image of a user's mouth, uploading the pointcloud image to a computer having one or more dental design software programs loaded thereon or available remotely through an Internet connection, and producing a software version of the oral appliance from the pointcloud image. The software version of the oral appliance may then be uploaded to a 3D printer, followed by 3D printing the upper generally arched-shaped member, the lower generally arched-shaped member, the lower right molar and pre-molar extension, the lower left molar and pre-molar extension, the upper right molar and pre-molar extension, and the upper left molar and pre-molar extension. Laser scanning images is a well-established practice in the medical industry. See for example the laser scanners available from Laser Design, Minneapolis, Minnesota (U.S.A.). See also U.S. Pat. Nos. 7,184,150; 7,153,135; and 9,522,054. In some cases, a 3D rendering may be made from a 2D image, such as a photograph or 2D drawing of a user's dentition. See for example U.S. Pat. Nos. 8,165,711 and 8,605,136. Intraoral imaging equipment, CAD/CAM and imaging analysis software are available from various sources, including Carestream Dental, 3Shape, Renishaw, 3M, and others.

Although the foregoing description is intended to be representative of apparatus, kits, and methods in accordance with the present disclosure, it is not intended to in any way limit the scope of the appended claims. For example, rather than scanning the user's mouth and/or dentition using a laser scanner wand, the more traditional method of first making an impression of a person's teeth and jaw set may be made, and from that, a physical plaster model, or impression created. Once the physical model is made, a laser scanner may scan the physical model to produce the software version, which may then be used to mold or 3D print the oral appliances of the present disclosure.

What is claimed is:

1. An oral appliance having moldable polymeric upper and lower arch-shaped members, the members being U-shaped in cross-section defining troughs configured to friction fit over a user's respective upper and lower dentitions, the upper arch-shaped member including pre-molar region and molar region, and the lower arch-shaped member including pre-molar region and molar region, comprising:
    a) the upper arch-shaped member comprising a palate extension having a length ranging from 2 mm to 20 mm, the palate extension configured to extend posteriorly along the user's palate from adjacent a rear of the user's upper central incisors to an arcuate distal edge;
    b) the lower arch-shaped member comprises integrally formed right molar extension, right pre-molar extension, left molar extension, and left pre-molar extension, each extension has a first height that increases uniformly from posterior to anterior of the lower arch-shaped member;
    c) the upper arch-shaped member comprises integrally formed right molar extension, right pre-molar extension, left molar extension, and left pre-molar extension, each extension has a second height that is constant from posterior to anterior of the upper arch-shaped member;
    d) so that when the user bites or clenches, left and right upper molar and pre-molar extensions impinge on left and right lower molar and pre-molar extensions, such impingement defining a gap between anterior portions of the upper and lower arch-shaped members, the gap having a height ranging from 6 mm to 15 mm;
    e) the left and right pre-molar extensions and the left and right molar extensions of the lower arch-shaped member are positioned such that each pre-molar extension and each molar extension are angled outwardly from posterior to anterior laterally at angle $\theta$ from a longitudinal axis of the pre-molar region and molar region thereof, providing extra lateral space for the user's tongue;
    f) the left and right pre-molar extensions and the left and right molar extensions of the upper arch-shaped member are positioned such that each pre-molar extension and each molar extension are angled outwardly from posterior to anterior laterally at angle $\beta$ from a longitudinal axis of the pre-molar region and molar region thereof, providing extra lateral space for the user's tongue;
    g) wherein the angles $\beta$ and $\theta$ independently range from 5 degrees to 30 degrees;
    h) wherein the respective pre-molar regions are configured to friction fit over the user's pre-molars, and the respective molar regions are configured to friction fit over the user's molars.

2. The oral appliance of claim 1 wherein the palate extension length ranges from 4 mm to 18 mm.

3. The oral appliance of claim 1 wherein the palate extension length ranges from 6 mm to 16 mm.

4. The oral appliance of claim 1 wherein the palate extension has a constant uniform thickness.

5. The oral appliance of claim 1 wherein the palate extension arcuate distal edge configured to extend laterally left and right from a central longitudinal axis of the upper arch-shaped member at least to respective left and right first premolars of the user.

6. The oral appliance of claim 1 wherein the palate extension arcuate distal edge configured to extend laterally left and right from a central longitudinal axis of the upper arch-shaped member at least to respective left and right second premolars of the user.

7. The oral appliance of claim 1 wherein the first height of each of the lower right and the lower left molar and pre-molar extensions increases from 1.5 mm to 20 mm.

8. A method comprising:
   a) inserting at least one or both of the upper and lower arch-shaped members of claim 1 into the user's mouth and fitting the upper arch-shaped member adjacent at least the portion of the interior and exterior surfaces of the user's upper dentition, fitting the palate extension against an anterior portion of the user's palate, and fitting the lower arch-shaped member adjacent at least the portion of the interior and exterior surfaces of the lower dentition; and
   b) the upper and the lower arch-shaped members over respective upper and lower dentitions.

9. The method of claim 8 further comprising adjusting one or more of:
   the upper arch-shaped member to fit adjacent at least the portion of the interior and exterior surfaces of the user's upper dentition,
   the lower arch-shaped member to fit adjacent at least the portion of the interior and exterior surfaces of user's lower dentition, and
   the palate extension to fit adjacent at least the anterior portion of the user's palate.

10. A kit comprising the upper and lower arch-shaped members of claim 1.

11. An oral appliance having moldable polymeric upper and lower arch-shaped members, the members being U-shaped in cross-section defining troughs configured to friction fit over a user's respective upper and lower dentitions, the upper arch-shaped member including pre-molar region and molar region, and the lower arch-shaped member including pre-molar region and molar region, comprising:
   a) the upper arch-shaped member comprising a palate extension having a length ranging from 2 mm to 20 mm, the palate extension configured to extend posteriorly along the user's palate from adjacent a rear of the user's upper central and lateral incisors to an arcuate distal edge;
   b) the lower arch-shaped member comprises integrally formed right molar extension, right pre-molar extension, left molar extension, and left pre-molar extension, each extension has a first height that increases uniformly from posterior to anterior of the lower arch-shaped member;
   c) the upper arch-shaped member comprises integrally formed right molar extension, right pre-molar extension, left molar extension, and left pre-molar extension, each extension has a second height that is constant from posterior to anterior of the upper arch-shaped member;
   d) so that when the user bites or clenches, left and right upper molar and pre-molar extensions impinge on left and right lower molar and pre-molar extensions, such impingement defining a gap between anterior portions of the upper and lower arch-shaped members, the gap having a height ranging from 6 mm to 15 mm;
   e) the left and right pre-molar extensions and the left and right molar extensions of the lower arch-shaped member are positioned such that each pre-molar extension and each molar extension are angled outwardly from posterior to anterior laterally at angle $\theta$ from a longitudinal axis of the pre-molar region and molar region thereof, providing extra lateral space for the user's tongue;
   f) the left and right pre-molar extensions and the left and right molar extensions of the upper arch-shaped member are positioned such that each pre-molar extension and each molar extension are angled outwardly from posterior to anterior laterally at angle $\beta$ from a longitudinal axis of the pre-molar region and molar region thereof, providing extra lateral space for the user's tongue;
   g) wherein the angles $\beta$ and $\theta$ independently range from 5 degrees to 30 degrees;
   h) wherein the respective pre-molar regions are configured to friction fit over the user's pre-molars, and the respective molar regions are configured to friction fit over the user's molars.

12. The oral appliance of claim 11 wherein the palate extension length ranges from 4 mm to 18 mm.

13. The oral appliance of claim 11 wherein the palate extension length ranges from 6 mm to 16 mm.

14. The oral appliance of claim 11 wherein the palate extension has a constant uniform thickness.

15. The oral appliance of claim 1 wherein the palate extension arcuate distal edge configured to extend laterally left and right from a central longitudinal axis of the upper arch-shaped member at least to respective left and right first premolars of the user.

16. The oral appliance of claim 1 wherein the palate extension arcuate distal edge configured to extend laterally left and right from a central longitudinal axis of the upper arch-shaped member at least to respective left and right second premolars of the user.

17. The oral appliance of claim 11 wherein the first height of each of the lower right and the lower left molar and pre-molar extensions increases from 1.5 mm to 20 mm.

18. A method comprising:
   a) inserting at least one or both of the upper and lower arch-shaped members of claim 11 into the user's mouth and fitting the upper arch-shaped member adjacent at least the portion of the interior and exterior surfaces of the user's upper dentition, fitting the palate extension against an anterior portion of the user's palate, and fitting the lower arch-shaped member adjacent at least the portion of the interior and exterior surfaces of the lower dentition; and
   b) the upper and the lower arch-shaped members over respective upper and lower dentitions.

19. The method of claim 8 further comprising adjusting one or more of:
   the upper arch-shaped member to fit adjacent at least the portion of the interior and exterior surfaces of the user's upper dentition,
   the lower arch-shaped member to fit adjacent at least the portion of the interior and exterior surfaces of user's lower dentition, and
   the palate extension to fit adjacent at least the anterior portion of the user's palate.

20. A kit comprising the upper and lower arch-shaped members of claim 11.

* * * * *